United States Patent [19]

Beech, Jr. et al.

[11] Patent Number: 5,138,102

[45] Date of Patent: Aug. 11, 1992

[54] REACTOR QUENCHING FOR CATALYTIC OLEFIN HYDRATION IN ETHER PRODUCTION

[75] Inventors: James H. Beech, Jr., Wilmington, Del.; James A. Stoos, Blackwood; Stephen S. F. Wong, Medford, both of N.J.; Sergei Yurchak, Media, Pa.

[73] Assignee: Mobil Oil Corporation, Fairfax, Va.

[21] Appl. No.: 794,634

[22] Filed: Nov. 18, 1991

Related U.S. Application Data

[63] Continuation of Ser. No. 557,242, Jul. 25, 1990, abandoned.

[51] Int. Cl.$^5$ .............................................. C07C 41/06
[52] U.S. Cl. ...................................... 568/695; 422/194; 568/897; 568/697
[58] Field of Search ...................... 568/695, 897, 697

[56] References Cited

U.S. PATENT DOCUMENTS

| | | |
|---|---|---|
| 4,182,914 | 1/1980 | Imaizumi . |
| 4,334,890 | 6/1982 | Kochar et al. ...................... 568/895 |
| 4,579,984 | 4/1986 | Neier et al. ........................ 568/897 |
| 4,857,664 | 8/1989 | Huang et al. . |

FOREIGN PATENT DOCUMENTS 323268  7/1989  European Pat. Off. ............ 568/695

OTHER PUBLICATIONS

Hougen et al., Chemical Process Principles, Part 3, Kinetics & Catalysis, John Wiley, New York, 1947, pp. 1031–1033.

*Primary Examiner*—Howard T. Mars
*Attorney, Agent, or Firm*—Alexander J. McKillop; Charles J. Speciale; L. G. Wise

[57] ABSTRACT

A process for production of ether by hydration and etherification of olefinic feedstock containing at least one lower alkene by contacting the olefinic feedstock and water in a plurality of catalytic reaction zones containing porous solid metal oxide acidic olefin hydration and etherification catalyst under olefin hydration and etherification conditions. Improved operation is achieved by recovering a first effluent stream from at least one fixed bed hydration zone, splitting the first effluent stream into a product recovery stream and a plurality of recycle streams, and passing at least a portion of cooled recycle streams comprising olefin, alcohol and ether in effluent stream component proportions for quenching at least one fixed bed reaction zone to control temperature of hot effluent from a preceding reaction zone.

7 Claims, 1 Drawing Sheet

REACTOR QUENCHING FOR CATALYTIC OLEFIN HYDRATION IN ETHER PRODUCTION

This is a continuation of copending application Ser. No. 07/557,242, filed on Jul. 25, 1990 now abandoned.

REFERENCE TO COPENDING APPLICATION

This application is related to cofiled U.S. patent application Ser. No. 07/557,241 filed Jul. 25, 1990, Improved Catalytic Olefin Hydration with Ether Production by J. Beech et al.

BACKGROUND OF THE INVENTION

This invention relates to olefin hydration, especially for production of di-isopropyl ether (DIPE) from $C_3+$ olefinic feedstocks. Particularly, the invention relates to a novel technique for operating a fixed bed multizone reactor with solid hydration catalyst.

The need to eliminate lead-based octane enhancers in gasoline has provided incentive for development of processes to produce high octane gasolines blended with lower aliphatic alkyl ethers as octane boosters. Supplementary fuels are being vigorously developed in the petroleum refining industry. Lower molecular weight alcohols and ethers such as isopropyl alcohol (IPA), isopropyl t-butyl ether (IPTBE), and diisopropyl ether (DIPE) are in the boiling range of gasoline fuels and are known to have a high blending octane number. They are useful octane enhancers. In addition, by-product propene (propylene) from which IPA and DIPE can be made is usually available in a fuels refinery, typically as a $C_3+$ aliphatic stream rich in propene and propane. The petrochemicals industry also produces mixtures of light olefin streams in the $C_2$–$C_7$ molecular weight range and the conversion of such streams or fractions thereof to alcohols and/or ethers can also provide products useful as solvents and blending stocks for gasoline.

Adapting available refinery feedstock to produce these oxygenates simultaneously as octane enhancers can involve two different olefin hydration and etherification processes, i.e. propene hydration-etherification to give DIPE and IPA. Accordingly, a challenge is provided to explore these processes to discover how they may be integrated in a manner more beneficial to the production of high octane gasoline.

Catalytic hydration of olefins to provide alcohols and ethers is established technology for production of the IPA and DIPE and is of significant commercial importance. Representative olefin hydration processes are disclosed in U.S. Pat. Nos. 4,334,890 (Kochar); 3,912,463 (Kozlowski et al.); 4,042,633 (Woods); 4,499,313 (Okumura et al.); 4,886,918 (Sorensen et al).

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

Production of ether from secondary alcohols such as isopropanol and light olefins is known. As disclosed in U.S. Pat. No. 4,182,914 (Imaizumi), DIPE is produced from IPA and propylene in a series of operations employing a strongly acidic cation exchange resin as catalyst. Recently, processes for the direct hydration of olefins to provide alcohols and ethers using porous shape selective metallosilicate zeolite catalyst, such as zeolite Beta have been disclosed in U.S. Pat. No. 4,857,664 (Huang et al.), incorporated by reference. Prior processes for hydrating olefins have often been found to be inefficient with regard to catalyst life. Maldistribution of water and hydrocarbon reactants may cause deactivation, especially with solid metallosilicate catalysts having large pores (i.e. 7+ Angstroms) or medium pores (5–7 A°).

It is a main object of this invention to provide a process for production of oxygenated hydrocarbons by olefin hydration, such as alcohols and/or ethers in a more economical manner and with improved yields of ethers. It is another object of the present invention to provide an improved process for the production of isopropanol and di-isopropyl ether with increased catalyst life.

SUMMARY OF THE INVENTION

A novel process has been discovered for production ether/alcohol from lower olefins. In the preferred embodiments, di-isopropyl ether (DIPE) is produced by hydration of feedstock containing propene, which comprises contacting the propene feedstock and water in a catalytic reactor having a series of fixed bed hydration zones with porous solid acidic olefin hydration catalyst under olefin hydration conditions. Improved operation is achieved by recovering a first liquid effluent stream from the catalytic reactor; splitting the first liquid effluent stream into a liquid product recovery stream and a liquid recycle stream; cooling at least a portion of said liquid recycle stream; and passing the cooled liquid recycled stream as interstage quench between fixed bed hydration zones for controlling reaction temperature.

The preferred solid catalyst comprises acidic zeolite, such as zeolite Beta, and hydration zone conditions comprise temperature of about 50° to 220° C. Advantageously, total liquid recycle is combined with fresh feed at a weight ratio of about 2:1 to 10:1 recycle:feed. Typically, liquid product stream is separated into at least two streams for recycle to separate reaction zones, and wherein at least a portion of cooled liquid recycle is injected between separated fixed catalyst beds. The fixed bed hydration zones may be maintained in a vertical downflow reactor; and wherein the solid catalyst comprises at least one metal oxide catalyst.

These and other advantages and features of the invention will be seen in the description and drawing.

DETAILED DESCRIPTION OF THE INVENTION

Figure 1:
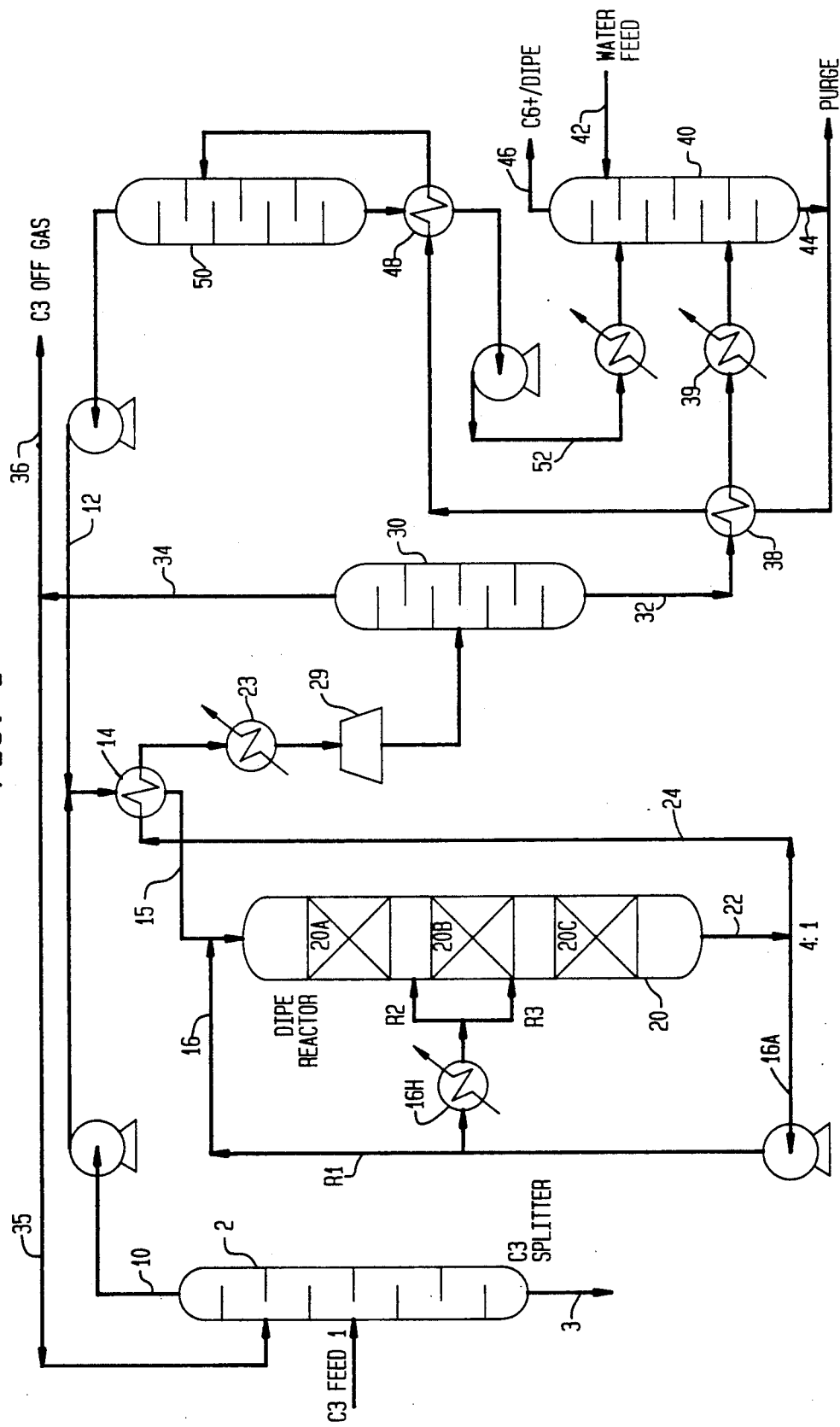
FIG. 1 is a schematic process flow diagram of the improved process.

The preferred embodiments of the invention are described with reference to propylene hydration and zeolite catalysts. Metric units and parts by weight are employed unless otherwise indicated.

The olefins hydration and etherification process employs the reaction of propylene with water catalyzed by strong acid to form isopropanol. Reaction may be allowed to continue in the hydration zone to form di-isopropyl ether. The operating conditions of the olefin hydration step include a temperature of about 50° to 450° C., preferably from about 100° to about 250° C. and most preferably from about 120° to about 220° C. The pressure is about 700 to 24000 kPa (100 to about 3500 psi, preferably about 500-2000 psi). Water to olefin reactant concentrations are maintained at mole ratio of about 0.1 to 30, preferably 0.3-5.

Olefin hydration to provide ethers and alcohols to produce DIPE and byproduct isopropyl alcohol (IPA) is described in U.S. Pat. Nos. 4,214,107; 4,499,313 incorporated herein by reference. The preferred catalytic methods for making DIPE employ porous solid acid catalysts, such as zeolites Y, Beta, ZSM-35 and/or MCM-22 aluminosilicate. DIPE etherification conditions may vary widely in choice of temperature, pressure and reaction time. The present process provides for reaction of propene with water in an adiabatic downflow reactor containing a fixed bed of zeolite Beta and operating pressure of at least 4000 kPa. However, it is understood that the unit operations described herein can be conducted with any number of specific process steps within the skill of the art.

The olefin hydration process of this invention are carried out in liquid phase, supercritical dense phase, or mixtures of these phases in continuous manner using a fixed bed flow reactor. Weight hourly space velocity, based on catalyst weight is maintained in the range of about 0.1 to about 10/hour when operating continuously.

Various modifications can be made within the inventive concept, especially with regard to reactor system configuration. Although a single reactor bed may be employed, it is advantageous to employ a series of fixed bed reactor units to permit adequate control of reaction conditions, especially temperature phase behavior and flow parameters.

It may be feasible to recover an unreacted olefin and recycle it to the reactor. Unconverted isopropanol recovered from the final reactor effluent may also be recycled to further conversion to ether.

The preferred hydration/etherification catalyst comprises acidic shape selective porous zeolite having a pore size of about 5-8 Angstroms, such as aluminosilicate zeolite Beta. Also, MCM-22, having pores similar to zeolite Beta and ZSM-5, is known for etherification catalysis.

Referring to FIG. 1 of the drawing, a process flow diagram depicts production of diisopropyl ether by hydration of fresh olefinic feedstock stream, which is introduced as a propane-propene mixture via inlet 1 to feed splitter tower 2 to recover a propane-rich bottoms stream 3. An overhead stream consisting essentially of propene ($C_3=$, propylene) is pumped along with water from stream 12 through heat exchanger 14 to bring the reactants and recycle stream 16 to the process conditions for etherification in vertical reactor 20 in contact with porous solid acidic olefin hydration catalyst.

The reactor vessel 20 contains a series of fixed bed adiabatic hydration reaction zones 20A, 20B, 20C maintained under olefin hydration conditions. Static mixers and liquid distributors may be employed before each bed to promote operation in a single homogeneous phase, as localized high concentrations of water or propylene are known to deactivate acidic catalysts (both zeolites and resins). Preferably, at least one hydration reaction zone contains porous zeolite catalyst, such as zeolite Beta.

A fluid handling system is operatively connected for recovering a liquid or supercritical dense phase reactor effluent stream 22 from the last zone 20C. This can be achieved by splitting effluent stream 22 into a liquid product recovery stream 24 and a liquid recycle stream 16A, which is recycled to the multizone reactor 20 as a plurality of flow-controlled recycle streams R1, R2, R3. Heat exchanger 16H cools the interstage quench streams R2, R3 below the process reaction, thus balancing the adiabatic heat of reaction from the preceding zone. Reactor 20 is operated continuously by passing the liquid recycle stream 16A substantially unfractionated. Reaction temperature can be controlled in zones 20B, 20C by varying the degree of cooling and/or flow rate of the recycle stream in unit 16H.

The amount of unfractionated liquid recycle stream 16 may be sufficient to maintain a substantially homogeneous single liquid reaction phase in the primary hydration zone 20A under reaction conditions. Use of DIPE, IPA containing product for quench will also promote single phase operation. The first liquid product stream 24 is passed via exchangers 14, 28 and fluid handling unit 29 to the product fractionation system, as described. Effluent stream 24 is fractionated in the product recovery system first in column 30 to recover ether-rich stream 32 and a propene-rich vapor stream 34, which may be recycled to tower 2 via line 35. Some of the steam may be purged from the system via line 36. It is advantageous to recover isopropanol for recycle to the reactor to provide isopropanol byproduct stream for further conversion to di-isopropyl ether. In the DIPE system depicted, unfractionated liquid recycle stream 16A is passed to reactor 20 at a rate which is about four times the total weight of propene and water reactants in the product recovery stream 24; the exact quantity depends an conversion targets, feed properties, etc.

Ether-rich stream 32 containing byproduct isopropanol, unreacted propene, water and $C_6+$ hydrocarbon oligomer is further separated after passing through heat exchangers 38, 39 to extractor unit 40, where it is contacted with fresh feed water 42 and water recycle stream 52 to extract isopropanol in an aqueous phase 44. A product stream 46 consisting essentially of DIPE and byproduct $C_6+$ propene oligomer is recovered from the extraction unit 40. The extract phase 44 is passed via exchangers 38, 48 to distillation column 50 to obtain an overhead isopropanol recycle stream 12 and liquid aqueous stream 52 for use in extraction unit 40.

The process flow scheme for olefin hydration to ethers over a zeolite Beta catalyst as disclosed utilizes product recycle and reactor quench for improved catalyst life and temperature control. The example system utilizes three catalyst beds in a single vertical reactor shell with mixing with inter-bed quench to reduce cost while controlling system phase behavior in comparison to other designs (tubular reactor).

The example shows improved catalyst life and yield benefits when recycling reactor product (pumparound) for propene hydration to di-isopropylether (DIPE) over typical porous acid solid catalyst. Product pumparound is advantageous as a means of controlling reactor temperature rise and therefore reduces equipment cost, as compared to a conventional isothermal tubular reactor or the like. The use of the product recycle for inter-bed quench eliminates inter-reactor coolers while giving benefits in control of phase behavior. The three beds are contained in a single reactor vessel. This reactor design is lower cost than other reactor designs.

This preferred process design, which is suitable for commercial design, utilizes feed purification, product recycle, and reactor quench for hydration of propene to DIPE to achieve high propylene conversion (~95% overall). The design also takes advantage of reactor recycle and quench with interstage mixing-distribution to provide reduced catalyst aging and reactor temperature control (heat removal).

In the following example, 65% zeolite Beta is used in extrudate form with alumina binder; however, other binders such as silica, zirconia, etc may be used. Continuous runs are made, with weight hourly space velocity of 0.33 charged to catalyst basis for propene. Unless otherwise indicated, reaction conditions include reactor inlet temperature of about 165° C. and pressure of about 10,000 kPa. Comparative runs include a single zone adiabatic downflow reactor with fixed bed extrudate catalyst. Tables 1 and 2 give data for a typical DIPE production system, based on 100 parts by weight of fresh propene feed.

TABLE 1

| | Stream Component Flowrates | | | | | | | | | | |
|---|---|---|---|---|---|---|---|---|---|---|---|
| | Stream No. | | | | | | | | | | |
| | 1 | 3 | 10 | 12 | 15 | 24 | 35 | 32 | 46 | 44 | 52 | 42 |
| $C_3=$ | 100 | 4.24 | 237.91 | 0.00 | 237.91 | 142.64 | 142.1400 | 0.498 | 0.498 | 0.000 | 0.00 | 0.00 |
| $C_3$ | 91.27 | 90.77 | 59.60 | 0.00 | 59.60 | 59.60 | 59.1020 | 0.498 | 0.498 | 0.000 | 0.00 | 0.00 |
| Water | | | | 50.12 | 50.12 | 32.67 | 0.0000 | 32.670 | 0.748 | 176.560 | 126.43 | 18.20 |
| IPA | | | | 51.37 | 51.37 | 51.62 | 0.0000 | 51.621 | 0.249 | 51.370 | 0.00 | 0.00 |
| DIPE | | Trace | | 5.49 | 5.49 | 106.23 | 0.0022 | 106.234 | 100.748 | 5.490 | 0.00 | 0.00 |
| $C_6=+$ | | Trace | | 0.50 | 0.5 | 12.22 | 0.0002 | 12.220 | 11.720 | 0.498 | 0.00 | 0.00 |
| TOTAL | 191.27 | 95.01 | 297.51 | 107.48 | 404.99 | 404.99 | 201.2500 | 203.740 | 114.463 | 233.92 | 126.43 | 18.20 |

TABLE 2

| | Reactor Recycle/Quench Component Flowrates | | |
|---|---|---|---|
| | R1 Recycle to First Bed | R2 Recycle to Second Bed | R3 Recycle to Third Bed |
| $C_3=$ | 498.8 | 71.6 | 79.3 |
| $C_3$ | 208.2 | 29.9 | 33.2 |
| Water | 114.0 | 16.5 | 18.2 |
| IPA | 180.3 | 25.9 | 28.7 |
| DIPE | 371.1 | 53.1 | 59.1 |
| $C_6=+$ | 42.6 | 6.2 | 6.7 |
| TOTAL | 1415 | 203.2 | 225.2 |
| Average Temperature, °F. (°C.) | 330 (165° C.) | 129 (54° C.) | 129 (54° C.) |
| T, °F./bed | 20 (11° C.) | 20 (11° C.) | 20 (11° C.) |
| Bed Inlet Temp. °F. (SOC) | 310 (155° C.) | 310 (155° C.) | 310 (155° C.) |
| Bed Inlet Temp. °F. (EOC) | 350 (177°) | 350 (177°) | 350 (177°) |
| Bed Inlet Temp. °F. (SOC) | 330 (165° C.) | 330 (165° C.) | 330 (165° C.) |
| Bed Inlet Temp. °F. (EOC) | 370 (188° C.) | 370 (188° C.) | 370 (188° C.) |

In fixed bed hydration of propene to di-isopropylether (DIPE), catalyst aging has been found to limit cycle length and catalyst life during single pass operation. When effluent recycle with mixing and quenching are employed, propene conversion and DIPE yield increase and aging is significantly reduced. This effect is unexpected, since pump-around type of reactor operation (i.e., back mixed) generally reduces conversion compared to plug flow (single pass). Catalyst life is increased compared to conventional process flow schemes. Product pumparound recycle is ordinarily expected to lower yields (back-mixed versus plug flow) and reduce catalyst life (coke/polymer formation). The opposite occurs in both instances.

This advantage in yield and catalyst aging is unexpected. Product recycle is believed to improve overall distribution in the reactor due to higher flux and improving phase behavior (a single liquid phase versus water-rich and water-lean phases). The increased DIPE at the reactor inlet might act as a solvent to remove coke precursors. Temperature control by product recycle quench is also a primary benefit for process with a small window of operation.

This flow scheme provides significant benefits beyond simple heat control. It is possible to adjust pumparound composition by adjusting reactor effluent temperature, separating out a water rich phase, and recycling a separated ether-rich phase which may further improve performance. This same effect in water reduction might also be accomplished by reducing the water content or amount of the IPA/water recycle from distillation.

A theoretical explanation for the observed increase in yields results from the strong solvents isopropanol/ether saturating the catalyst pores. This prevents the formation of any separate water or olefin phases in the pores during operation. The aqueous or hydrocarbon phases can cause catalyst deactivation. The water phase may attack the crystalline structure of the catalyst, while a highly olefinic phase would deactivate the catalyst via rapid coke formation. The isopropanol/ether mixture also allows controlled quantities of water and propylene to be present homogeneously in the catalyst pores, which allows the reactions to proceed properly at reaction temperature. For the recycle technique to be effective, the recycled liquid must dissolve the water and olefin present in fresh feedstock and the quench must be used with good mixing and distribution.

While the invention has been described by specific examples and embodiments, there is no intent to limit the inventive concept except as set forth in the following claims.

We claim:
1. A process for the production of diisopropyl ether by hydration and etherification of fresh olefinic feedstock containing propene with water, which comprises the steps of:
   contacting the propene feedstock and water with porous solid acidic olefin hydration/etherification catalyst in a series of primary and secondary fixed bed adiabatic reaction zones under olefin hydration and etherification conditions with interstage mixing and redistribution, including at least one reaction zone containing shape selective medium pore zeolite comprising zeolite Beta;

recovering a first fluid effluent stream from at least one fixed bed hydration zone;

splitting said first fluid effluent stream into a product recovery stream and a fluid recycle stream;

cooling and passing a portion of said fluid recycle stream comprising olefin, alcohol and ether in effluent stream component proportions for quenching said secondary fixed bed reaction zone along with hot effluent from the primary reaction zone, wherein the recycle stream consists essentially of about 0-10 wt % water, 20-60 wt % propene, 20-30 wt % di-isopropyl ether, and 10-15 wt % isopropanol and is fed to the primary fixed bed reaction zone along with fresh propene feedstock and fresh water in amount sufficient to maintain a substantially homogeneous single fluid reaction phase in said first reaction zone.

2. The process of claim 1 wherein the reaction conditions comprise temperature controlled in the range of about 120° to 220° C.

3. The process of claim 1 wherein said product stream is fractionated to recover a di-isopropyl ether stream, a byproduct stream containing isopropanol and an unreacted propene stream; and wherein said isopropanol byproduct stream is recycled to said primary reaction zone for further conversion to di-isopropyl ether.

4. The process of claim 3 wherein interstage static mixers and liquid distributors are used for controlling composition/phase behavior in the reactor.

5. In the process for the production of diisopropyl ether by hydration and etherification of feedstock containing propene, which comprises contacting the propene feedstock and water in a catalytic reactor having a series of fixed bed reaction zones with porous solid acidic olefin hydration/etherification catalyst having a pore size of about 5-8 Angstroms under olefin hydration and etherification conditions, the improvement which comprises:

recovering a reactor effluent stream from said catalytic reactor;

splitting said reactor effluent stream into a product recovery stream, a first recycle stream and a second recycle stream which recovery and recycle streams consist essentially of olefin, alcohol and ether in effluent stream proportions;

cooling and passing the first recycle stream as interstage quench between fixed bed reaction zones; and passing the second recycle stream to a first catalytic reaction zone in said series of fixed bed reaction zones for mixing with feedstock propene and water.

6. The process of claim 5 wherein said solid catalyst consists essentially of zeolite Beta, and wherein the reaction zone conditions comprise temperature of 120° to 220° C.

7. The process of claim 5 wherein said fixed bed reaction zones are maintained in a vertical downflow reactor.

* * * * *